(12) United States Patent
Yuan et al.

(10) Patent No.: US 7,012,106 B2
(45) Date of Patent: *Mar. 14, 2006

(54) REINFORCED IMPLANTABLE MEDICAL DEVICES

(75) Inventors: Jenny J. Yuan, Neshanic Station, NJ (US); Joseph H. Contiliano, Stewartsville, NJ (US); Yufu Li, Bridgewater, NJ (US); Zhigang Li, Hillsborough, NJ (US); Mark B. Roller, North Brunswick, NJ (US); Murty N. Vyakarnam, Edgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 427 days.

This patent is subject to a terminal disclaimer.

(21) Appl. No.: 10/401,469

(22) Filed: Mar. 28, 2003

(65) Prior Publication Data

US 2004/0254639 A1    Dec. 16, 2004

(51) Int. Cl.
*A61F 2/00* (2006.01)
*C08G 63/06* (2006.01)

(52) U.S. Cl. .............. 523/115; 525/450; 525/937; 528/354; 524/414; 524/423; 524/425; 524/433

(58) Field of Classification Search ........... 523/115; 528/354; 525/450, 937; 524/414
See application file for complete search history.

(56) References Cited

U.S. PATENT DOCUMENTS

| 4,643,734 | A |   | 2/1987  | Lin |
| 4,645,503 | A |   | 2/1987  | Lin et al. |
| 5,108,755 | A |   | 4/1992  | Daniels et al. |
| 5,509,913 | A | * | 4/1996  | Yeo ........................ 604/364 |
| 5,552,454 | A |   | 9/1996  | Kretschmann et al. |
| 5,679,723 | A |   | 10/1997 | Cooper et al. |
| 5,681,873 | A |   | 10/1997 | Norton et al. |
| 5,725,541 | A | * | 3/1998  | Anspach et al. ............. 606/151 |
| 5,747,390 | A |   | 5/1998  | Cooper et al. |
| 5,766,618 | A |   | 6/1998  | Laurencin et al. |
| 5,955,529 | A |   | 9/1999  | Imai et al. |
| 5,962,007 | A |   | 10/1999 | Cooper et al. |
| 5,971,987 | A |   | 10/1999 | Huxel et al. |
| 6,165,486 | A |   | 12/2000 | Marra et al. |
| 6,331,313 | B1 | * | 12/2001 | Wong et al. ................ 424/427 |
| 2002/0072797 | A1 |   | 6/2002 | Hays et al. |
| 2003/0040695 | A1 | * | 2/2003 | Zhao et al. .................. 604/15 |
| 2003/0233095 | A1 | * | 12/2003 | Urbanski et al. ............ 606/72 |
| 2004/0001890 | A1 | * | 1/2004 | Rosenblatt et al. ......... 424/469 |
| 2004/0193285 | A1 | * | 9/2004 | Roller et al. ............. 623/23.75 |

FOREIGN PATENT DOCUMENTS

| DE |     27 42 128 A1 | 9/1977 |
| EP |     0 714 666 A1 | 6/1996 |
| WO | WO 90/01342 A1   | 2/1990 |
| WO | WO 00/01426 A1   | 1/2000 |

OTHER PUBLICATIONS

Technical Literature: Leray, J. L.; Chabot, F.; De Charentenay, F. X.; Christel, P.; Sedel, L.; and Vert, M, Biodegradeable Composite Materials for Bone Surgery., Trans. Soc. Biomater., 1, 70 (1977).

* cited by examiner

Primary Examiner—Tae H. Yoon

(57) ABSTRACT

The present invention is directed to reinforced, biocompatible, biodegradable compositions suitable for use in implantable medical devices and medical devices made at least in part from such compositions, where the compositions include a biocompatible, biodegradable polymer; a biocompatible, biodegradable wax; and greater than about 30 weight percent of an inorganic filler material.

20 Claims, 2 Drawing Sheets

REINFORCED IMPLANTABLE MEDICAL DEVICES

FIELD OF THE INVENTION

The present invention relates to reinforced, biocompatible, biodegradable materials suitable for use in the fabrication of implantable medical devices (IMDs) and biodegradable implantable medical devices fabricated at least in part from such materials.

BACKGROUND OF THE INVENTION

Implantable medical devices (IMDs) have been widely used for more than 40 years in various surgical applications. For example, in fracture fixation operations, IMDs are used to address bone fractures by attaching a reinforcing rod or a plate or a cage to a fractured bone so that the broken ends may be stabilized to promote fusion and consequent healing. In sport medicine area, IMDs are used to repair and augment soft tissues, such as anterior cruciate ligament (ACL) replacement. IMDs such as screws are used to affix autografts, allografts, xenografts, or bone fragments to bone structure of a patient. In the case of ACL procedure, the torn ACL is replaced by inserting an IMD in the form of interference screw into a bone tunnel to secure one end of a replacement graft in place.

Metal implants have often been used because of their high stiffness and strength. However, several issues still remain. Metal implants, being much stiffer than bone, become the primary load-bearing member thereby protecting the bone from stress, which results in undesirable stress shielding. It is often necessary to perform a second surgical procedure to remove metal implants after the bone tissues have healed.

The use of biodegradable materials, materials that degrade in the body and then are either absorbed into or excreted from the body, has the potential to eliminate the necessity of a second operation and help alleviate the negative effects of stress shielding. Biodegradable polymeric materials have been used as IMDs in the form of pins, rods, anchors, screws, staples, and fasteners for a variety of medical applications. However, relatively low stiffness and strength of biodegradable devices compared with metallic implants has limited their use to low-load bearing applications or non-load bearing applications.

Inorganic fillers have been used as reinforcement to enhance the mechanical properties of biodegradable polymeric materials. Homopolymers and copolymers of L-lactic, DL-lactic and glycolic acids reinforced with tricalcium phosphate ranging from 0 to 40 percent by weight were studied. Typically, composites of this nature exhibit increased stiffness, but are characteristically brittle.

In U.S. Pat. No. 6,165,486 (to Marra, et al.), hydroxyapatite (HA) granules were incorporated into the blends of poly(caprolactone) and poly(D,L-lactic-co-glycolic) acid for replacing, augmenting or serving as a substitute for hard tissue such as bone. Marra teaches that HA in the range of about 0 to 25 weight percent can be incorporated into the composition. Marra also states, "If the tissue being replaced, augmented, or substituted or the device being formed does not benefit from incorporation of a mineralized component, it is advisable to substantially omit hydroxyapatite from the blend. This is because incorporation of hydroxyapatite results in a more "brittle" device. Minimal or no hydroxyapatite is desirable where a brittle characteristic renders the device or article less useful e.g., sutures, anchors, fixation systems such as sutures, suture anchors, staples, surgical tacks, clips, plates and screws. It is also advisable to avoid large concentrations (i.e., above 10% by weight) of hydroxyapatite soft tissue applications such as tissue used to substitute or augment breast tissue."

Due to the inherent brittleness and lower strength of these materials, ceramic filler-reinforced biodegradable polymers have often been used in non- or low-load bearing applications such as bone filler or cement.

In another aspect of medical procedures, the movement of a surface of an implantable device with respect to tissue is important in reducing damage to both the material of the surface and to the tissue. Damage to tissue as a result of this tissue-drag friction causes inflammation and pain to the patient and leads to a longer recovery time. High friction between the surface material and blood may result in clotting and subsequent occlusion of a blood vessel. Friction may also damage the material, thus rendering it ineffective or shortening its useful life.

In summary, the inherent brittleness and high stiffness of biodegradable composite systems know to date have limited their usefulness for applications in certain IMDs. In addition, there is a need for methods of reducing device drag in biodegradable composite IMDs while maintaining the degradable nature of the devices.

SUMMARY OF THE INVENTION

The present invention is directed to reinforced, biocompatible, biodegradable compositions suitable for use in implantable medical devices and medical devices made at least in part from such compositions, where the compositions comprise a biocompatible, biodegradable polymer; a biocompatible, biodegradable wax; and greater than about 30 weight percent of an inorganic filler material. Devices according to the present invention containing relatively high levels of filler material when compared to conventional devices and possess properties such as good elongation to failure, i.e. they are flexible and are non-brittle, and high lubricity.

DETAILED DESCRIPTION OF THE INVENTION

Figure 1:
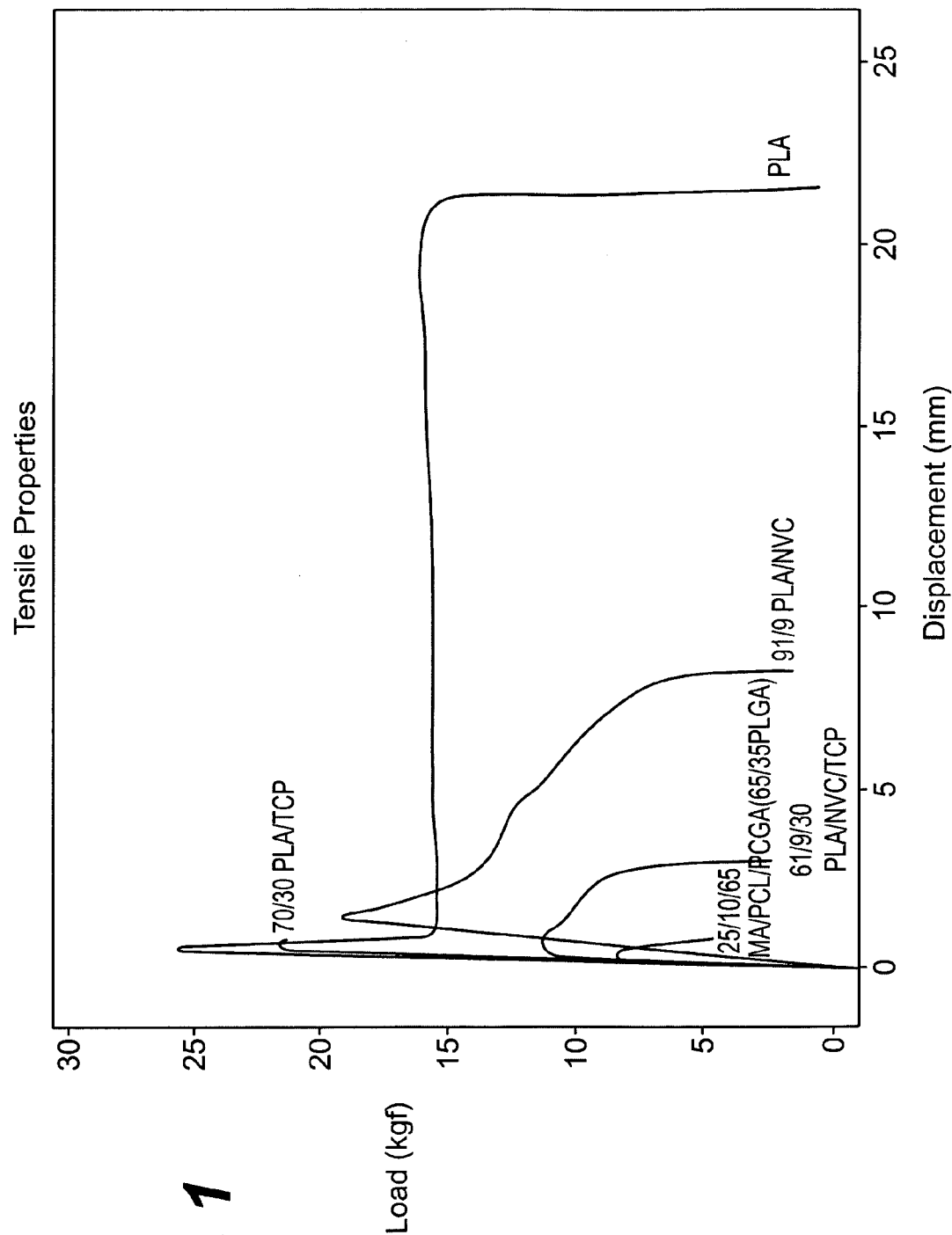
FIG. 1 is a stress-strain curve of the tensile tests of four different materials.

This present invention relates to biocompatible, biodegradable polymeric composite compositions possessing improved elongation to failure and lower surface friction. In addition to a biocompatible, biodegradable polymer suitable for use in medical devices, the compositions comprise a polymeric wax component and greater than about 30 percent by weight of an inorganic filler material used for the purpose of providing reinforcement properties to the materials when utilized in the fabrication of medical devices. The invention also relates to implantable medical devices that are fabricated at least in part from such composition and which possess properties such as good elongation to failure, i.e. they flexible and are non-brittle, and high lubricity.

Implantable medical devices where compositions of the present invention may be useful include, but are not limited to, absorbable maxillofacial bone fixation plates, absorbable bone screws or other fastening devices, absorbable surgical clips and staples, absorbable devices with living hinges, and absorbable bone fixation rods and screws. Potential also exists in applications where two articulating surfaces come together and need a certain lubricity, such as rivet/pin constructs and expanding sleeve or collar devices.

In order to possess bulk properties suitable for processing into medical devices, the composite materials preferably comprise a continuous, biodegradable polymer phase, with the inorganic filler and biodegradable wax components being dispersed substantially homogenously there through. The individual components may be blended together such that the filler and wax are homogeneously dispersed through the polymer phase. Such blends then may be further processed by standard methods of compounding, for example extrusion or batch compounding, following by chopping of the compounded material to form pellets and the like of the homogenous blend. The pellets then may be used to prepare medical devices according to the invention, for example by extrusion or compression molding. Alternately, the individual components may be added directly to a compounding and molding apparatus, for example an extruder having the proper mixing screw configuration so as to homogenously blend the components in the extrusion barrel, with the extruder being fitted with the appropriate die to form medical devices according to the invention. Once having the benefit of this disclosure, one skilled in the art would be able to select the proper parameters and specific apparatus required for the particular blend of components and medical device being fabricated.

The continuous polymer phase comprises a high molecular weight, biocompatible, biodegradable polymer. High molecular weight polymers, are defined herein, comprise polymers with an inherent viscosity (IV) of greater than about 2.0 dl/g when measured in chloroform at 25° C. By biodegradable, it is meant that the polymer may be degraded or otherwise broken down in the body such that the components of the degraded polymer may be absorbed by or otherwise passed from the body.

Examples of suitable biocompatible, biodegradable polymers that could be used according to the present invention include, without limitation, polymers selected from the group consisting of aliphatic polyesters, poly(amino acids), copoly(ether-esters), polyalkylenes oxalates, polyamides, poly(ethylene glycol), poly(iminocarbonates), polyorthoesters, polyoxaesters, polyamidoesters, polyoxaesters containing amine groups, poly(anhydrides), polyphosphazenes, biopolymers, and copolymers and blends thereof.

Aliphatic polyesters useful according to the present invention include, but are not limited to, homopolymers and copolymers of lactide (which includes lactic acid, D-,L- and meso lactide), glycolide (including glycolic acid), epsilon-caprolactone, para-dioxanone (1,4-dioxan-2-one), trimethylene carbonate (1,3-dioxan-2-one), alkyl derivatives of trimethylene carbonate, monoglyceride polyesters, and polymer blends thereof.

Preferred polymers utilized in the invention comprise homopolymers of lactide (PLA) and homopolymers of glycolide (PGA). More preferred are copolymers of PLA and PGA (PLGA), such copolymers comprising from about 80 to about 95 mole percent PLA.

The wax component of the present invention is a low molecular weight biocompatible, biodegradable polymer with a low coefficient of friction. Low molecular weight polymers are defined herein comprise polymers with an Inherent Viscosity (IV) of less than about 0.7 dl/g when measured in chloroform at 25° C. Preferably, the IV is between about 0.3 and 0.5 dl/g when measured in chloroform at 25° C. For the purposes of this invention, a wax is defined as a polymer that is a solid at room temperature, has a relatively low melting point, e.g. preferably below 100° C., that is slippery and plastic when, and fluid when melted.

Examples of suitable biocompatible, biodegradable waxes that could be used include, without limitation low molecular weight polymers selected from the group consisting of aliphatic polyesters, poly(amino acids), copoly(ether-esters), polyalkylenes oxalates, polyamides, poly(ethylene glycol), poly(iminocarbonates), polyorthoesters, polyoxaesters, polyamidoesters, polyoxaesters containing amine groups, poly(anhydrides), polyphosphazenes, biopolymers, and copolymers and blends thereof.

Aliphatic polyesters which can be made into a wax, as defined herein, include, but are not limited to, homopolymers and copolymers of lactide (including lactic acid, D-,L- and meso lactide), glycolide (including glycolic acid), ε-caprolactone, para-dioxanone (1,4-dioxan-2-one), trimethylene carbonate (1,3-dioxan-2-one), alkyl derivatives of trimethylene carbonate, monoglyceride polyesters, and blends thereof.

For example, monoglyceride polyester (MGPE) materials suitable for this invention include biocompatible, biodegradable aliphatic polyester waxes made by the polycondensation of monoalkanoyl glycerides and common dicarboxylic acids These MGPEs have an aliphatic polyester backbone with pendant fatty acid ester groups and exhibit relatively low melting points ($T_m < 100°$ C). Preferred waxes preferably have a melting point of below about 80° C., more preferably about 45° C. to 60° C.

Among the preferred wax materials are copolymers of lactide (PLA) and glycolide (PGA) (PLGA); epsilon-caprolactone (PCL) and lactide (PCLA); and epsilon-caprolactone and para-dioxanone (PDO) (PCDO). A preferred wax material is a copolymer of 95 mole percent PCL and about 5 mole percent PDO (95/5 PCDO).

The most preferred wax material comprises a copolymer of epsilon-caprolactone and glycolide. This family of polymers is more fully disclosed in U.S. Pat. No. 4,994,074, issued Feb. 19, 1991, assigned to Ethicon Inc., which is hereby incorporated herein by reference as if set forth in its entirely. Most preferred are copolymers comprising about 90 mole percent epsilon-caprolactone (PCL) and 10 mole percent glycolide (PGA) (90/10 PCGA).

The biocompatible, biodegradable inorganic fillers of the current 20 invention can be fine powders of ceramics comprising mono-, di-, tri-, α-tri-, β-tri-, and tetra-calcium phosphate, hydroxyapatite, fluoroapatites, calcium sulfates, calcium fluorides, calcium oxides, calcium carbonates, magnesium calcium phosphates, bioglasses, or mixtures thereof.

As noted above, composite materials of this invention can be melt processed by numerous methods to prepare a vast array of useful devices. The compositions may be injection or compression molded to make implantable medical devices for various surgical applications. Examples of such devices include reinforcing rods, plates, or cages used to aid in the stabilization of fractured bone. Devices also include fixation devices, e.g. screws, pins, and anchors, and expanding sleeve or collar devices, all used to repair and/or augment soft tissues or to affix autografts, allografts, xenografts, or bone fragments to the bone structure of a patient.

Figure 2:
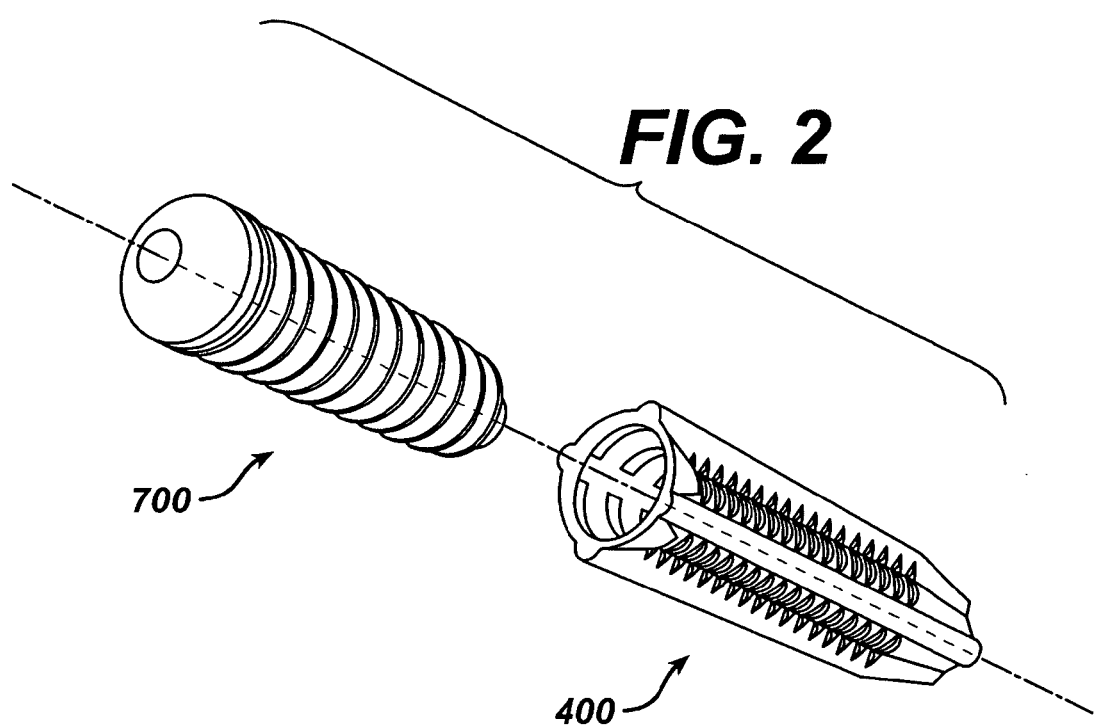
FIG. 2 is medical device of the present invention.

FIG. 2 is an exemplary medical device formed using the composition of the present invention. The device is a graft ligament anchor. The design of the anchor components are disclosed in U.S. patent application Ser. No. 09/966,766, entitled "Graft Ligament Anchor and Method for Attaching a Graft Ligament to a Bone", filed Sep. 28, 2001, the disclosure of which is incorporated by reference as if set forth in its entirety. The anchor comprises radially-expandable sheath 400 and sheath-expanding element 700. Other devices where compositions of the present invention may be used will be readily apparent to those skilled in the art once having the benefit of this disclosure.

Various bioactive agents such as proteins (including short chain peptides), growth agents, chemotatic agents and therapeutic agents can be added to the polymer or wax prior or during the time of blending to make the implantable medical devices of the present invention. In general, bioactive agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives such as rapamycin; muscle relaxants; parasympatholytics; psychostimulants; sedatives; tranquilizers; naturally derived or genetically engineered proteins, growth factors, polysaccharides, glycoproteins or lipoproteins; oligonucleotides; antibodies; antigens; cholinergics; chemotherapeutics; hemostatics; clot dissolving agents; radioactive agents; and cystostatics.

Growth factors include bone morphogenic proteins (i.e. BMPs 1–7), bone morphogenic-like proteins (i.e. GFD-5, GFD-7 and GFD-8), epidermal growth factor (EGF), fibroblast growth factor (i.e. FGF 1–9), platelet derived growth factor (PDGF), insulin like growth factor (IGF-I and IGF-II), transforming growth factors (i.e. TGF-$\beta$I-III), and vascular endothelial growth factor (VEGF).

The following examples are illustrative of the principles and practice of this invention, although not limited thereto. Numerous additional embodiments within the scope and spirit of the invention will become apparent to those skilled in the art once having the benefit of this disclosure. Unless stated otherwise, the Inherent Viscosity (IV) of the polymers and waxes disclosed herein were measured in chloroform at 25° C.

EXAMPLE 1

Compounding a composite blend of hydroxyapatide (HA), poly(epsilon-caprolactone) (PCL), and a 65/35 copolymer of lactide (PLA) and glycolide (PGA), or 65/35 poly(DL-lactide-co-glycolide) (65/35 PLGA).

91.5 grams of HA (Aldrich, Milwaukee, Wis.), 36.6 grams of 65/35 PLGA (BPI, Birmingham Polymers Inc., Birmingham, Ala., IV=0.66 dl/g) and 238.0 grams of PCL (Aldrich, Milwaukee, Wis., Molecular weight 42,500–65,000) were weighted out separately. The resultant weight ratio of the three components was 25/10/65. A model REE6 Prep-Mixer (Brabender, South Hakensack, N.J.) with cam blades was chosen to compound the blend. The PLGA, PCL and HA were fed into the mixing bowl sequentially.

The compounding process conditions were as follows: 1) mixer was preheated to 180° C., 2) blade speed set to 50 rpm, and 3) mixing time was 15 minutes after all the materials were fed. After compounding, the mixture was cooled, ground using a Wiley grinder, The ground material then was dried in a vacuum oven at 55° C. for 48 hours under a vacuum of 1 Torr and then stored at room temperature under vacuum for future processing.

EXAMPLE 2

Injection-Molding of tensile testing coupons using the material compounded in Example 1.

Tensile testing coupons (ASTM type V) of the material made in Example 1 were formed by injection molded using a 35-ton injection-molding machine (model NN35M14, Niigata LTD, Niigata, Japan). The processing conditions were as follows: 1) temperature profile 200, 230, 230, 220° C. from rear to nozzle, 2) injection pressure 26,640 psi, 3) holding pressure 20,980 psi, 4) injection speed set to 200 mm/second, 5) total time of injection and holding segments 2.5 seconds, and 6) cooling time 25 seconds.

EXAMPLE 3

Compounding a composite blend of tricalcium phosphate (TCP), poly(lactide) poymer (PLA), and a 90/10 wax of epsilon-caprolactone (PCL) and glycolide (PGA), or 90/10 poly(caprolactone-co-glycolide) (90/10 PCGA).

PLA polymer (Purac, Gorinchem, The Netherlands, IV=2.37 g/dl) and 90/10 PCGA wax (Ethicon, Incorporated, Somerville, N.J., IV=0.3–0.5 g/dl) were dry premixed in the weight ratio of 61/9. An 18-mm co-rotation twin-screw extruder (Model micro 18 GL/35, Leistritz, Somerville, N.J.) was used in the compounding process. The PLA/PCGA premix was fed using a gravimetlic feeder at a feed rate of 3.47 lbs/hr. The TCP powder (CAM Implants, Leiden, The Netherlands) was fed using a second gravimetric feeder at a feed rate of 1.53 lbs/hr. The resulting blend was 30 weight percent TCP, 6.3 weight percent PCGA, and 63.7 weight percent PLA (or 30/70 TCP/(9/91 (PCGA)/PLA).

The compounding process conditions, using a low to medium shear screw design, were as follows: 1) temperature profile from hopper to die was 100, 195, 195, 195, 190, 190, 190° C., 2) screw speed 150 rpm, 3) total feed rate 5 lbs/hr, 4) melt pressure about 630 psi, and 5) torque about 38 percent. The extrudate was cooled using an air cooling conveyer, pelletized and stored at room temperature under vacuum for future processing.

EXAMPLE 4

Compounding a blend of poly(lactide) (PLA), and a 90/10 wax of epsilon-caprolactone (PCL) and glycolide (PGA), or 90/10 poly(caprolactone-co-glycolide) (90/10 PCGA).

PLA polymer and 90/10 PCGA wax as described in Example 3 were dry premixed in the weight ratio of 91/9. The 18-mm co-rotation twin-screw extruder from Example 3 was used in the compounding process. The PLA/PCGA premix was fed using a gravimetric feeder at a feed rate of 5.0 lbs/hr.

The compounding process conditions, using a low to medium shear screw design, were the same as Example 3, except melt pressure was about 650 psi, and torque was about 32 percent. The extrudate was cooled using an air cooling conveyer, pelletized and stored at room temperature under vacuum for future processing. The resulting blend was 91/9 PLA/(90/10 PCGA).

EXAMPLE 5

Compounding a composite blend of tricalcium phosphate (TCP) and poly(lactide) polymer (PLA).

PLA polymer and TCP as described in Example 3 were used, as was the 18-mm co-rotation twin-screw extruder. The PLA was fed using a gravimetric feeder at a feed rate of 2.091 lbs/hr. The TCP powder was fed using a second gravimetric feeder at a feed rate of 0.909 lbs/hr. The resulting blend was 30 weight percent TCP, and 70 weight percent PLA (or 30/70 TCP/PLA).

The compounding process conditions, using a low to medium shear screw design, were as follows: 1) temperature profile from hopper to die was 190, 200, 190, 190, 190, 200, 200° C., 2) screw speed 250 rpm, 3) total feed rate 3 lbs/hr, 4) melt pressure about 1,700 psi, and 5) torque about 85 percent. The extrudate was cooled using an air cooling conveyer, pelletized and stored at room temperature under vacuum for future processing.

EXAMPLE 6

Injection-Molding of tensile testing coupons using the material compounded in Examples 3, 4, and 5.

Tensile testing coupons (ASTM type V) of the materials made in Examples 3, 4, and 5 were injection molded using the 35-ton injection molding machine described in Example 2. Neat PLA, as described in Example 3 also was injection molded.

The processing conditions were as follows: 1) temperature profile 350, 390, 400, 400° F. from rear to nozzle, 2) injection pressure 26,640 psi, 3) holding pressure 20,970 psi, 4) injection speed set to 200 mm/second, 5) total time of injection and holding segments 5 seconds, and 6) cooling time 25 seconds.

EXAMPLE 7

Tensile properties of the materials injection molded in Examples 2 and 6.

The ASTM tensile type V tensile coupons injection molded in Examples 2 and 6 were tested in tension using an Instron 4201 tested with Instron series IX data analysis software. A video-extensometer was used for elongation measurement. Tensile stress-strain curves for all or the materials are shown on FIG. 1. The figure shows the neat PLA had a yield point and a strain to failure of about 150 percent.

The addition of 30 weight percent TCP to PLA, or 30/70 TCP/PLA, significantly reduced the failure strain to about 3 percent, and the composite broke with no yielding behavior. So, the addition of TCP to PLA made the PLA more brittle.

The addition of 9 weight percent 90/10 PCGA wax to the PLA polymer, or 91/9 PLA/(90/10 PCGA), also showed a reduced strain to failure. This material had a yield point, and the strain to failure was about 50 percent. It is apparent that the addition of wax into PLA made the PLA more brittle.

In the fourth material system, in which 30 weight percent TCP and 9 weight percent PCGA wax were added to PLA polymer, the stress-strain curve showed a yield point and a strain to failure of 20 percent. This result was a surprise as the 30/70 TCP/(9/91 (PCGA)/PLA) composite had much higher value of strain to failure compared to 30/70 TCP/PLA. It is apparent that instead of increasing the brittleness of the 30/70 TCP/PLA material, the addition of wax toughened the composite.

EXAMPLE 8

Process for forming exemplary medical device using the material of the present invention.

Bioabsorbable graft ligament anchor components as shown in FIG. 2 were manufactured using an injection molding process.

The polymer used to make the radially-expandable sheath elements 400 was PLA, (Purac, Gorinchem, The Netherlands, IV of 1.87 dL/g as measured in chloroform). Sheath-expanding elements 700 were formed using the PLA described in this example, and 30/70 TCP/(9/91(PCGA)/ PLA), 91/9 PLA/(90/10 PCGA), and 30/70 TCP/PLA described in Examples 3, 4, and 5, respectively.

All parts were injection molded using the 35-ton injection-molding machine described in Example 2. The processing conditions for the expandable sheath elements were as follows: 1) temperature profile 300, 400, 410, 420° F. from rear to nozzle, 2) injection pressure 15000 psi, 3) holding pressure 13700 psi, 4) injection speed set to 200 mm/second, 5) total time of injection and holding segments 2 seconds.

EXAMPLE 9

Torque forces required to engage the graft ligament anchor device of Example 8.

The torque forces required to insert the sheath-expanding elements into the radially-expandable sheaths described in Example 8 were measured. The method was as follows: Pilot holes, 11.5 mm in diameter, were drilled in a model bone material (#25 Sawbone, Pacific Research, Vashon, Wash.). Four GORE-TEX Joint Sealants (¼-inch diameter), sold by W. L. Gore & Associates, Inc., Elkton, Md., were placed in each quadrant of the pilot hole to simulate hamstring tendons. A radially-expandable sheath was inserted inside the pilot hole so that the joint sealants were between the sheath and the walls of the pilot hole. The distal end of a sheath-expanding element was inserted into the central lumen of the expandable sheath. A digital torque gauge (Digital Torque Gauge Model TMG, IMADA Incorporated, Northbrook, Ill.) was used to measure the insertion torque. The digital torque gauge was a driver connected to a torque meter so that the torque was measured while driving the sheath-expanding element into the expandable sheath.

The driver was disposed into the central cannulation of the sheath-expanding element.

The peak insertion torque values required to drive the expanding element into the sheath central lumen for PLA, 30/70 TCP/(9/91(PCGA)/PLA), and 91/9 PLA/(90/10 PCGA) expanding elements were 30+, 15, and 12 in-lb, respectively. The 30/70 TCP/PLA expanding sheath was brittle and broke during the insertion, so no peak torque was determined for this material.

We claim:

1. A biocompatible, biodegradable composition suitable for use in implantable medical devices, comprising:
   a biocompatible, biodegradable polymer,
   a aliphatic polyester wax selected from the group consisting of homopolymers and copolymers of lactide, glycolide, epsilon-caprolactone, para-dioxanone, trimethylene carbonate, alkyl derivatives of trimethylene carbonate and monoglyceride polyesters; and
   at least 30 percent of an inorganic filler material based on the weight of the composition.

2. The composition of claim 1 wherein the biodegradable polymer is selected from the group consisting of aliphatic polyesters, poly(amino acids), copoly(ether-esters), polyalkylenes oxalates, polyamides, poly(ethylene glycol), poly(iminocarbonates), polyorthoesters, polyoxaesters, polyamidoesters, polyoxaesters containing amine groups, poly(anhydrides), polyphosphazenes, biopolymers and copolymers thereof.

3. The composition of claim 2 wherein the aliphatic polyester is selected from the group consisting of homopolymers and copolymers of lactide, glycolide, epsilon-caprolactone, para-dioxanone, trimethylene carbonate, alkyl derivatives of trimethylene carbonate and monoglyceride polyesters.

4. The composition of claim 3 wherein the aliphatic polyester comprises a copolymer of from about 80 to 99 mole percent lactide and glycolide.

5. The composition of claim 4 wherein the aliphatic polyester has an inherent viscosity of greater than about 2.0 g/dl as measured in chloroform at 25° C.

6. The composition of claim 1 wherein the aliphatic polyester wax comprises a copolymer of from about 90 to about 10 mole percent epsilon-caprolactone and glycolic acid.

7. The composition of claim 6 wherein the wax has an inherent viscosity of less than about 0.7 g/dl as measured in chloroform at 25° C.

8. The composition of claim 1 wherein the inorganic filler material is selected from the group consisting of mono-, di-, tri-, α-tri-, β-tri-, and tetra-calcium phosphate, hydroxyapatite, fluoroapatites, calcium sulfates, calcium fluorides, calcium oxides, calcium carbonates, magnesium calcium phosphates and bio-glasses.

9. The composition of claim 8 wherein the inorganic filler material comprises β-tricalcium phosphate.

10. A biodegradable implantable medical device, comprising a biocompatible, biodegradable composition, the composition comprising:
 a biocompatible, biodegradable polymer,
 a aliphatic polyester wax selected from the group consisting of homopolymers and copolymers of lactide, glycolide, epsilon-caprolactone, para-dioxanone, trimethylene carbonate, alkyl derivatives of trimethylene carbonate and monoglyceride polyesters; and
 at least 30 percent of an inorganic filler material based on the weight of the composition.

11. The medical device of claim 10 wherein the biodegradable polymer is selected from the group consisting of aliphatic polyesters, poly(amino acids), copoly(ether-esters), polyalkylenes oxalates, polyamides, poly(ethylene glycol), poly(iminocarbonates), polyorthoesters, polyoxaesters, polyamidoesters, polyoxaesters containing amine groups, poly(anhydrides), polyphosphazenes, biopolymers and copolymers thereof.

12. The medical device of claim 11 wherein the aliphatic polyester is selected from the group consisting of homopolymers and copolymers of lactide, glycolide, epsilon-caprolactone, para-dioxanone, trimethylene carbonate, alkyl derivatives of trimethylene carbonate and monoglyceride polyesters.

13. The medical device of claim 12 wherein the aliphatic polyester comprises a copolymer of from about 80 to 99 mole percent lactide and glycolide.

14. The medical device of claim 13 wherein the aliphatic polyester has an inherent viscosity of greater than about 2.0 g/dl as measured in chloroform at 25° C.

15. The medical device of claim 10 wherein the aliphatic polyester wax comprises a copolymer of from about 90 to about 10 mole percent epsilon-caprolactone and glycolic acid.

16. The medical device of claim 15 wherein the wax has an inherent viscosity of less than about 0.7 g/dl as measured in chloroform at 25° C.

17. The medical device of claim 10 wherein the inorganic filler material is selected from the group consisting of mono-, di-, tri-, α-tri-, β-tri-, and tetra-calcium phosphate, hydroxyapatite, fluoroapatites, calcium sulfates, calcium fluorides, calcium oxides, calcium carbonates, magnesium calcium phosphates and bio-glasses.

18. The medical device of claim 17 wherein the inorganic filler material comprises β-tricalcium phosphate.

19. The medical device of claim 10 selected from the group consisting of reinforcing rods, plates, cages, screws, pins, anchors, expanding sleeves and expanding collars.

20. The medical device of claim 19 wherein the anchor comprises a radially-expandable sheath and a sheath-expanding element.

* * * * *